United States Patent [19]

Matsumura

[11] Patent Number: 5,175,004
[45] Date of Patent: Dec. 29, 1992

[54] PROPAGATABLE, NEW COMBINANT CELLS FOR CELLULAR REPLACEMENT THERAPY

[76] Inventor: Kenneth N. Matsumura, 2107 Dwight Way, Berkeley, Calif. 94704

[21] Appl. No.: 290,431

[22] Filed: Dec. 27, 1988

[51] Int. Cl.$^5$ .................. A01N 1/00; A61K 35/12; C12N 15/02

[52] U.S. Cl. .................. 424/520; 424/556; 424/572; 435/1; 435/172.2; 435/240.26; 604/48; 935/52; 935/59; 935/89; 935/93

[58] Field of Search .................. 435/1, 172.2, 240.26; 424/93, 520, 556, 572; 935/52, 59, 89, 93, 45, 99, 102, 106; 604/48

[56] References Cited

U.S. PATENT DOCUMENTS

| | | |
|---|---|---|
| 4,195,125 | 3/1980 | Wacker .................. 935/102 |
| 4,439,521 | 3/1984 | Archer et al. .................. 435/1 |
| 4,645,669 | 2/1987 | Reid .................. 435/1 |
| 4,963,489 | 10/1990 | Naughton et al. .................. 435/1 |

FOREIGN PATENT DOCUMENTS

| | | |
|---|---|---|
| 1201396 | 4/1986 | Canada . |
| 0251106 | 1/1988 | European Pat. Off. . |

OTHER PUBLICATIONS

M. J. Narasimhan et al., *Int. Cong. Ser.-Excerpta Med.* 413, 521-528, 1977.
Hightower et al., in Snay et al., (EDS.), *Techniques in Somatic Cell Genetics,* Plenum Press, New York, 1982, pp. 255-267.
Narasimhan et al., *Chem. Abs.* 89, 22072q, 1978.
Wacker et al., *Chem. Abs.,* 86, 118951q, 1977.
Veomett et al., *Proc. Natl. Acad. Sci., USA,* 71, 1999-2002, 1974.

*Primary Examiner*—David Saunders

[57] ABSTRACT

A method for creating a propagatable, new combinant cell with differentiated function to replenish dwindling number of similar cells in diseased subjects. The new combinant cell is obtained by 1) removing a nucleated cell, which is of the same differentiative phenotype as the diseased cells, from a subject and isolating therefrom a karyoplast, 2) isolating from a source other than said subject a proliferation-prone cell which is of the same differentiative phenotype or which is predestined to become the same phenotype as the diseased cells and isolating therefrom a cytoplast, 3) fusing the cytoplast and karyoplast to form a propagatable, new combinant cell, 4) propagating the combinant cell in culture, and 5) transplanting the combinant cells into said subject. In another embodiment the karyoplast donor is histocompatible to said subject. In yet another embodiment a whole cell is used in lieu of a karyoplast for fusion with the cytoplast.

3 Claims, No Drawings

PROPAGATABLE, NEW COMBINANT CELLS FOR CELLULAR REPLACEMENT THERAPY

BACKGROUND OF THE INVENTION

1. Field of the Invention

Some diseases are caused by an insufficiency in the number of certain types of cells which died for various reasons. In cirrhosis of the liver, a lack of hepatocytes in sufficient number to detoxify accumulating metaholic poisons causes coma. In Addison's disease, a lack of adrenal cortical cells causes death unless the diseased individual receives steroid hormones that are usually provided by these cortical cells. In Type I diabetes mellitus, a lack of pancreatic islet beta cells causes death unless the diseased individual receives insulin that is usually provided by these beta cells.

Sometimes, an insufficiency in the number of certain cells is not caused by disease but is the result of an adverse side effect to chemotherapy of diseases like cancer. Drugs and radiation used to kill cancer cells also kill normal hemopoietic marrow and lymphopoietic cells and patients die from the lack of blood cells.

Unfortunately, unlike the lower forms such as the planarian worms, mammals can not readily grow replacement cells because, generally, mature, differentiated cells do not self-reproduce much if at all. Mammals also reject any transplant of replacement cells if such cells are taken from anyone else than self. (One exception to this rule is where cells are transplanted between identical twins (syngeneic transplant)). Rejection occurs because, like fingerprints, every individual has a unique histocompatibility protein called transplantation antigen on the membrane surface of his/her cells. Every individual also has immunologic defense cells called lymphocytes which are capable of recognizing as foreign any cells from other individuals. Any transplanted cells possessing foreign transplantation antigens are promptly rejected and killed by these lymphocytes. The uniqueness of each individual's antigen is the result of the uniqueness of the individual's desoxyribonucleic acid (DNA). The transplantation antigen is made employing a messenger ribonucleic acid (mRNA) template which in turn is a complementary copy of the DNA's histocompatibility locus. With the exceptions of identical twins and members of a closely inbred strains of animals, who are genetically identical (i.e., possess identical DNA's), everyone else has his/her own unique code at the histocompatibility locus.

Since at this time it is not possible to make mature, differentiated cells to replicate themselves in order to replenish their number, and since transplanting replacement cells from other individuals is fraught with much difficulty and risks, I thought that it could be desirable to construct a new cell which: 1) possessed transplantation antigenicity compatible with the diseased or deficient individual, and 2) possessed function of the cells whose number is lacking in the diseased or deficient individual. A large number of such cells can then be successfully transplanted into the diseased or deficient individual and correct the insufficiency.

In setting about on the task of constructing a new cell with above requirements, I relied on the following hypotheses.

A. The specificity of the transplantation antigen on the cell surfaces is determined by the nuclear DNA.

B. Except for the germ cells, nuclear DNA's of every cell in the body, whether from skin epithelium, mesenchymal fibroblast, intestine, myocyte, hepatocyte, or pancreatic islet, all contain the same genetic code.

C. Although the DNA's of different tissues are identical, different parts of the DNA are being expressed and so different proteins are being caused to be synthesized; different proteins make one cell to be, for example, myotube and another to be hepatocyte.

D. There can be present in the cytoplasm, factors which direct adjacent nuclear DNA to continue the expression that differentiates the cell as, for example, kidney or liver; similarly, there can be present in the cytoplasm, factors that encourage DNA to frequently enter the mitotic cycle, i.e., making the cell self-replicating.

2. Description of the Prior Art

Constructing a new cell with new properties has become possible owing to the technology of fusing two whole cells or fusing nucleus (karyoplast) of one cell with cytoplasm (cytoplast) of another cell. I believe the credit for pioneering in this art goes to Henry Harris (1965. Nature, London, 206: 583-1966. J. Cell Sci. 1: 1-1966. Proc. Roy. Soc. Brit. 166: 358-) and to D. M. Prescott (1974. Proc. Natl. Acad. Sci. 71(5): 1999-2002). An improved method for fusing cells and their components using polyethylene glycol (PEG) has been described by R. L. Davidson (1978. Natl. Cancer Inst. Monofr. 48: 21-30). Some of the hypotheses described in the preceding paragraph on which this invention is predicated have been tested and investigated by various workers (R. L. Davidson, cited above; Choy-Pik Chiu and Helen Blau, 1984. Cell 37: 879-887; Inge Schwag and O. Luger, 1980. Differentiation 16: 93-99). Their work gave me greater confidence that my ideas would work. However, I had no assurance of success without actually practicing my methods because there are contradicting findings among the work just cited and in the rest of the literature on the mechanisms of differentiation and cell proliferation.

SUMMARY OF THE INVENTION

I have developed a method for replacing desired cells in subjects in whom said desired cells have become depleted comprising removing a nucleated cell from said subject and isolating therefrom a karyoplast, obtaining from a source other than said subject a proliferation-prone cell which is of the same phenotype or which is pre-destined to become the same phenotype as said desired cells and isolating therefrom a cytoplast, then fusing said karyoplast with said cytoplast, propagating the combinant cell product of said fusion in culture, and transplanting said combinant cells into said subject. In another embodiment of the invention, said combinant cells are transplanted into a different subject having histocompatibility characteristic identical or only weakly varying from the karyoplast donor, who in this embodiment does not necessarily have any depletion of said desired cells.

DESCRIPTION OF THE SPECIFIC EMBODIMENTS

Karyoplast utilizable in this invention may be obtained from whole cells by various methods, such as those of David M. Prescott (a. 1973. In Methods in Cell Biology (D. M. Prescott, ed.). 7: 189-202. Acad. Press, New York. 1974. Proceedings of the National Academy of Sciences 71(5): 1999-2002) or Joseph J. Lucas and Joseph R. Kates (1976. Cell 7: 397-405). Improvements and modification from these standard methods are described in more recent literature which are easy to find. Karyoplast of Prescott is basically the whole nucleus within its nuclear membrane with small bits of cytoplasm adherent to it. Karyoplast is extruded out from a whole cell using centrifugation in presence of cytochalasin B.

Cytoplast utilizable in this invention may be obtained by various methods such as those of Prescott (cited above) or Lucas and Kates (also cited above) or T. V. Gopalakrishnan and W. French Anderson (1979. Proceedings of the National Academy of Sciences 76 (8): 3932-3936). Improvements and modifications from these standard methods are described in more recent literature which are easy to find. Cytoplast is what results after a whole cell extrudes off the karyoplast in above methods and it consists of most of the cytoplasm of the cell enveloped in cell membrane.

Karyoplast and cytoplast may be fused to create a new combinant cell by various methods such as that of Davidson (cited above) or that of Prescott (cited above) or Gopalakrishnan (also cited above). Davidson describes a method using polyethylene glycol (PEG) as an agent to induce fusion in large quantity between karyoplast and cytoplast or between cells. PEG 1000 is particularly good as fusing agent. The use of inactivated Sendai virus (see Gopalakrishnan) is an alternative means for fusion. The fusion methodology is quite standard and routine now.

Since this invention relies upon the cytoplasm exerting influence on a strange nuclear DNA fused upon it, such cytoplasm must meet certain requirement to be utilizable in this invention. The new combinant cell must be capable of exhibiting the desired functional or differentiative phenotype (e.g., hepatocyte, pancreatic islet beta cell, hemopoietic stem cells which may be more pluripotent but still restricted in potential development only to those of blood cells). To assure this goal, cells from which cytoplast is obtained must be of the same phenotype or be pre-destined to become the same phenotype as the desired cells. By the term "pre-destined" cell I mean a cell with morphology not showing complete differentiation but which nevertheless has been induced (e.g., by electrical and chemical influences) to differentiate into a certain phenotype. These are usually embryonic cells which have emerged from germ layers to begin forming organs in the embryo. Such cells continue to look less differentiated while they are proliferating in mitogen-rich environment but when they stop or slow their division, their full differentiation characteristics become visible or evident. Others have used a similar term, "pre-determined".

It is desirable that the new combinant cell easily proliferate to propagate itself. To aim toward this goal, the cell from which cytoplast is obtained should best be one which is already cycling, i.e., regularly engaging in DNA synthesis. Most adult cells are not cycling and are not easily induced into cycling even if mitogen-rich medium is provided in culture. Fetal cells of various organs and stem cells, like hemopoietic, intestinal crypt, and epidermal basal stem cells, are cycling and can be referred to as being proliferation-prone.

The cell providing the karyoplast is obtained from the subject in whom certain desired cells have become depleted. The following is the list, in the order of decreasing preference, of the types of cells which can provide the nuclear material. 1. If available, the desired cells which is in short supply would best serve to provide the karyoplasts that would be used to create a new combinant cell that can propagate to increase the number of desired cells in short supply. 2. One can also extract karyoplasts from undifferentiated germ-layer cells from which the desired cells originated (e.g., intestinal cells originated from the endodermal layer—the originating germ layer for any given cell is described in most embryology text books). 3. Less desirably, one can also extract karyoplasts from other cells that share the same germ-layer origin as the desired cell (e.g., .if the desired cell is endodermally derived, then other cells which are also endodermally derived). 4. Finally, one can use a fibroblast or other cells from the subject. The latter two choices do not always lead to success.

Where one employs a karyoplast from the germ layer, one preferably fuses it first to a cytoplast(s) of a differentiated cell of the phenotype desired. Thereafter, one fuses one or more cytoplasts from proliferating cells that are pre-destined to become the phenotype desired.

To allow the new combinant cell to propagate, it should be cultured under conditions conductive to rapid proliferation (e.g., plentiful supply of oxygen and nutrients) and in mitogen-rich medium (high concentration of amino acid, vital growth factors and vitamins, supplementation with fetal bovine serum and embryo extract). When cells propagated in this manner are ready for transplantation, they can be placed in maintenance type medium low in mitogens (e.g., a chemically defined medium like Basal Medium with supplementation only of adult serum).

The new combinant cell so propagated and now in sufficient number, can be transplanted into the subject from whom the original karyoplast was obtained. In fact, if the subject has an identical twin, such cells can also be transplanted into the twin. With mild immunosuppression, such cells can be transplanted into other unrelated individuals who differ with the subject, histocompatibility-wise, only weakly. By the term weakly, I mean something comparable to less difference than at H-2 locus in the mice (e.g., difference at H-4 or a comparable locus). The idea here is that one can utilize the thoughts behind tissue type (HLA) matching when looking for a donor of a transplant. Better the histocompatibility match between the donor and recipient of transplant, less immunosuppression is required. However, many successful (permanently) transplants have occurred between donors and recipients who had some degree of mis-matching. I envision that a tissue factory called "orplant" (a term I coined in 1963 from the words, organ (manufacturing) plant) can manufacture perhaps 20 different tissue types for any one kind of organ (e.g., 20 different histocompatibility tissue types for islet beta cells). Cells manufactured in such orplants do not have to be customized to be identical in histocompatibility antigenicity to the prospective transplant recipient. Instead, a diseased transplant recipient can choose from the 20 off-the-shelf tissue types the type that most closely matches his/her own tissue type. Subsequent to transpantation, such a recipient can receive a mild immunosuppression for an adequate length of time to keep the transplant from being rejected. Not infrequently, once the transplant establishes itself in the recipient, immunosuppressive drugs can be discontinued after a few months or a year without causing rejection of the slight mis-matched transplant.

It then becomes clear from the foregoing that karyoplasts may be obtained not only from cells of the subject in whom certain desired cells have become depleted but also from cells which are sufficiently histocompatible to said subject (e.g., HLA matched). In this application, such usable cells are said to be "histocompatible".

Pancreatic islet cells and other endocrine cells can be transplanted via inoculum into the portal circulation (nests of such cells survive in the liver), subcutaneously, or intraperitoneally. Hepatocytes can be transplanted via inoculum into the portal circulation or intraperitoneally. Muscle cells can be transplanted as tissue, or as inoculum into muscle tissue. Some other epithelial cells, like from the kidney, would best be grown together with associative mesenchymal cells in organ culture into three-dimensional framework of a miniature organ, which can then be heterotopically implanted near an arterial blood supply (such as in omental sac or under the capsule of the kidney) where it can grow and mature into an auxiliary organ, especially in the presence of humoral factors that encourage the growth of such implant. Such humoral factors can be found in those who have undergone partial nephrectomy (for kidney growth factor) or hepatectomy (for liver growth factor). One technique for organ culture is that employing Gelfoam (Registered Trademark of Upjohn Company, Kalamazoo, Mich.), a sterile collagen foam (See Montgomery, R. K.et al. 1983. Organotypic Differentiation of Trypsin-dissociated Fetal Rat Intestine. Dev.Biology 100: 181-189).

In forming an organ culture, one does not have to use combinant cells for every element of the organ. For example, fibroblast cells (a connective stromal element of an organ) does not have to he combinant because such cells, in contrast to mature epithelial cells, are always capable of proliferation. Only those cell elements that lack the capability to proliferate need to be made combinant. Therefore, cells like fibroblasts can be simply obtained from the prospective recipient and mixed with other combinant cells into organ culture. These fibroblasts can be from a hollow needle biopsy of the organ. For example, if a diseased subject needs replenishment of his kidney tissue, one can obtain a plug of his own kidney. This plug can be enzymatically dissociated to obtain a mixture of cells some of which will be used to make combinant cells and others of which will be used without change (e.g., fibroblasts) in the organ culture. Needless to say, cells like fibroflasts do not need to be from the diseased subject provided they are histocompatible to the diseased subject.

As an aside here, people should he cautioned lest they think that individual cells in a diseased organ are diseased. For example, hepatic cells in a liver organ that is shrivelled up with cirrhosis are not diseased themselves. The liver organ is dysfunctional because of all the scar tissue within the organ (from repeated alcoholic injury) which disrupts the three-dimensional structure of the organ. The beta cells of a juvenile Type 1 diabetic are not diseased (there is nothing wrong with the nuclear material). For this reason, this type of diabetes does not have a strong heritable quality. In fact, the beta cells of Type II diabetics may also be perfectly healthy. In Type II diabetes, hypoglycemia seems to be due to humoral factors secreted by fat cells that block the action of insulin.

When the new combinant cell is first created, the cell membrane still contains transplantation antigens of the cytoplast source. Such antigens are gradually replaced by new antigens that complement the new nuclear DNA as the cell membrane undergoes repair and reconstruction. If the cell divides, this antigen replacement occurs more rapidly since new membrane material must be made.

There may be instances in which it would be advantageous to transplant the combinant cell immediately after fusion. In such instance, one needs to immunosuppress the transplant host temporarily until the antigenicity of the cell membrane has changed over.

Instead of fusing cytoplast with karyoplast extracted from whole cells, one can fuse several identical cytoplasts with a whole cell. The influence of the cytoplasm of the whole cell can be diluted by fusing several cytoplasts.

In the methods described above for extruding karyoplasts and cytoplasts, one can end up with a preparation contaminated with whole cells. One can separate out whole cells by serial plating (whole cells can adhere to surfaces much better than karyoplast, for example) and/or by sedimentation through a gradient of ficoll.

The following examples abe presented by way of illustration and are in no ways intended to be exhaustive of all the ways this invention can be practiced.

EXAMPLES

Example 1

To create new combinant cells expressing pancreatic functions, one takes cytoplasts from epithelial cells of the 13-day embryonic pancreas anlagen of rat of one inbred strain (see I. Parsa & E. Marsh. 1976. Long-term Organ Culture of Embryonic Rat Pancreas in a Chemically Defined Medium. Am. J. Path. 82(1): 119-127; 1970. Chemically-defined Medium for Organ Culture Differentiation of Rat Pancreas Anlage. Exp. Cell Res. 59: 171-175.). Karyoplasts are obtained from pancreatic islet beta cells of adult rat of a second inbred strain. The karyoplast is fused with a cytoplast using PEG 6000. The new combinant cells are propagated in culture. Cortisone is omitted from the culture medium if beta cells are desired. Finally, several million new combinant cells are injected into the portal veins of a diabetic rat of the second strain.

Example 2

To create new combinant cells expressing functions of pluripotent bone marrow stem cells, cytoplasts are obtained using cytochalasin B and centrifugation from pluripotent bone marrow stem cells of a rat fetus of one inbred strain (I. M. Hann et al. 1983. Development of Pluripotent Hematopoietic Progenitor Cells in the Human Fetus. Blood 62(1) 118-123). Karyoplasts are obtained from macrophages of a rat of a second inbred strain. A karyoplasts and a cytoplast is fused using PEG 1000. The new combinant cells are grow in semisolid culture and subsequently transplanted into the marrow of a rat of the second strain whose own marrow cells are first killed by radiation.

Example 3

To create a new combinant cells expressing hepatocyte functions, cytoplasts are obtained from fetal hepatocytes of a mouse of one inbred strain. Whole hepatocytes are obtained by standard collagenase dispersion method from an adult mouse of a second inbred strain. Such hepatocytes usually do not proliferate in culture. Using inactivated Sendai virus or PEG 1000, the whole hepatocytes are fused with cytoplasts in the ratio of at least 1:2 by having more than twice as many cytoplasts in the fusion chamber as whole cells. The new combinant cells are propagated in Medium 199 supplemented with 20% fetal bovine serum and 1% rat or chick embryo extract. Finally, the new combinant cells are injected (10 million cells weekly) into the portal vein of a mouse of the second inbred strain whose liver had been virtually decimated by a hepatotoxin.

Example 4

Also to create new combinant cells expressing hepatocyte functions, cytoplasts are obtained from neonatal and proliferating fetal hepatocytes of one inbred strain of mice. Whole undifferentiated, endodermal germ cell is obtained from a mouse of a second inbred strain. Using PEG 1000 or inactivated Sendai virus, the whole endodermal cells are fused with cytoplasts from neonatal hepatocytes in the ratio of at least 1:3. Resultant combinant cells are cultured in Medium 199 supplemented with 10% fetal bovine serum. Three days later, the new combinant cells are fused with cytoplasts from fetal hepatocytes in the ratio of at least 1:2. The new combinant cells are propagated in Medium 199 supplemented with 20% fetal bovine serum and 1% rat or chick embryo extract. Finally, the new combinant cells are injected (10 million cells weekly) into the portal vein of a mouse of the second inbred strain whose liver had been virtually decimated by a hepatotoxin.

Example 5

To practice the invention with kidney cells, cytoplasts are obtained from fetal (e.g., one half gestational) renal epithelial cells of one inbred mouse strain and fused with karyoplast or whole cells (3 cytoplasts: 1 whole cell) of the renal epithelial cells of a second inbred mouse strain. Resulting combinant cells are grown in organ culture together with other proliferating, non-renal epithelial cells found in the kidney which are obtained from the second inbred mouse strain. The organ-culture is continued until organo-typic structures are observed pieces of such tissues about 1 mm cube or less are transplanted under the kidney capsule of the mouse from the second inbred strain. Just prior to transplant, the recipient mouse undergoes removal of one kidney and one half of the other kidney.

Above examples were presented for the purpose of illustration and clarification and is in no way exhaustive of all the ways one can practice this invention. Modifications are also possible that fall within the scope of the claims below.

I claim:

1. A method for replenishing desired cells in a subject in whom desired cells have become depleted comprising:
   obtaining cells that are histocompatible to said subject and are of the same differentiative phenotype as the desired cells;
   extracting karyoplasts from said histocompatible cells;
   obtaining donor cells from the group consisting of cells which are regularly engaged in DNA synthesis and are of the same differentiative phenotype as the desired cells and
   committed progenitor cells of the desired cells;
   extracting cytoplasts from said donor cells;
   fusing said cytoplast to said karyoplast to form a combinant cell;
   propagating said combinant cells in tissue culture under conditions conducive to rapid cellular proliferation;
   transplanting said propagant cells into said subject.

2. A method for replenishing desired cells in a subject in whom desired cells have become depleted comprising:
   obtaining cells that are histocompatible to said subject and are of the same differentiative phenotype as the desired cells;
   obtaining donor cells from the group consisting of cells which are regularly engaged in DNA synthesis and are of the same differentiative phenotype as the desired cells and
   committed progenitor cells of the desired cells;
   extracting cytoplasts from said donor cells;
   fusing said cytoplast to said histocompatible cell to form a combinant cell;
   propagating said combinant cells in tissue culture under conditions conducive to rapid cellular proliferation;
   transplanting said propagant cells into said subject.

3. Method of claim 1 or 2 wherein said propagation of said combinant cells occurs in organ culture together with proliferating, associative mesenchymal cells which are histocompatible to said subject to form an organ.

* * * * *